(12) United States Patent
Feige et al.

(10) Patent No.: US 11,815,515 B2
(45) Date of Patent: Nov. 14, 2023

(54) METHODS TO PREDICT RISK OF AND TO STRATIFY SARCOPENIA AND NAD DEFICIENCY

(71) Applicants: UNIVERSITY OF SOUTHAMPTON, Southampton (GB); AGENCY FOR SCIENCE, TECHNOLOGY AND RESEARCH, Singapore (SG)

(72) Inventors: Jerome Feige, Crissier (CH); Keith Malcolm Godfrey, Ashurst (GB); Neerja Karnani, Singapore (SG); Eugenia Migliavacca, Lausanne (CH)

(73) Assignees: University of Southampton, Southampton (GB); Agency for Science, Technology and Research, Singapore (SG)

( * ) Notice: Subject to any disclaimer, the term of this patent is extended or adjusted under 35 U.S.C. 154(b) by 791 days.

(21) Appl. No.: 16/962,357

(22) PCT Filed: Jan. 14, 2019

(86) PCT No.: PCT/EP2019/050819
§ 371 (c)(1),
(2) Date: Jul. 15, 2020

(87) PCT Pub. No.: WO2019/141627
PCT Pub. Date: Jul. 25, 2019

(65) Prior Publication Data
US 2021/0072258 A1  Mar. 11, 2021

(30) Foreign Application Priority Data

Jan. 17, 2018 (EP) .................................... 18152186
Aug. 7, 2018 (EP) .................................... 18187656

(51) Int. Cl.
*G01N 33/68* (2006.01)
*A23L 33/105* (2016.01)
*A23L 33/15* (2016.01)

(52) U.S. Cl.
CPC ........ *G01N 33/6887* (2013.01); *A23L 33/105* (2016.08); *A23L 33/15* (2016.08);
(Continued)

(58) Field of Classification Search
CPC ........... G01N 33/6887; G01N 2800/10; G01N 2800/50; G01N 2800/52; A23L 33/105; A23L 33/15; A23V 2002/00
See application file for complete search history.

(56) References Cited

U.S. PATENT DOCUMENTS 4,060,638 A    11/1977 Anderson
2006/0111443 A1  5/2006 Fukushima et al.
(Continued)

FOREIGN PATENT DOCUMENTS

CN    102802626    11/2012
EP    2269607      1/2011
(Continued)

OTHER PUBLICATIONS

Slupsky et al., Investigations of the Effects of Gender, Diurnal Variation, and Age in Human Urinary Metabolomic Profiles, Sep. 15, 2007, Analytical Chemistry, vol. 79, No. 18, pp. 6995-7004. (Year: 2007).*

(Continued)

*Primary Examiner* — Jennifer Wecker
*Assistant Examiner* — Kathryn Elizabeth Limbaugh
(74) *Attorney, Agent, or Firm* — K&L Gates LLP

(57) ABSTRACT

The present invention relates in general to the field of muscle disease. In particular, the invention relates to a method for determining if a subject has sarcopenia or has an increased (Continued)

risk of developing sarcopenia. A method of predicting the responsiveness of said subject to nutritional intervention is also provided.

19 Claims, 14 Drawing Sheets

(52) U.S. Cl.
CPC ...... *A23V 2002/00* (2013.01); *G01N 2800/10* (2013.01); *G01N 2800/50* (2013.01); *G01N 2800/52* (2013.01)

(56) References Cited

U.S. PATENT DOCUMENTS

| | | |
|---|---|---|
| 2007/0298998 A1 | 12/2007 | Paige et al. |
| 2013/0149388 A1 | 6/2013 | Mcclay et al. |

FOREIGN PATENT DOCUMENTS

| | | |
|---|---|---|
| FR | 3069434 A1 | 2/2019 |
| WO | 2010142750 | 12/2010 |
| WO | 2013188333 A1 | 12/2013 |
| WO | 2017108419 | 6/2017 |
| WO | 2017109195 | 6/2017 |

OTHER PUBLICATIONS

Yeong-Hau H. Lien "Looking for Sarcopenia Biomarkers" American Journal of Medicine, vol. 130, No. 5, May 2017, pp. 502-503.
Yanai, Hidekatsu "Nutrition for Sarcopenia" J Clin Med Res., 2015, vol. 7, No. 12, pp. 926-931.
Watanabe et al. "Serum C1q as a novel biomarker of sarcopenia in older adults" The FASEB Journal, 2015, vol. 29, pp. 1003-1010.
Kashani et al. "Evaluating Muscle Mass by Using Markers of Kidney Function: Development of the Sarcopenia Index" Crit Care Med, 2017, vol. 45, pages e23-e29.
Montes et al. "Potential early biomarkers of sarcopenia among independent older adults" Maturitas, 2017, vol. 104, pp. 117-122.
Rubbieri et al., "Techniques for the Diagnosis of Sarcopenia", Clinical Cases in Mineral and Bone Metabolism, vol. 11, Issue No. 3, 2014, pp. 181-184, XP055460606.
Pahor et al., "Sarcopenia: Clinical Evaluation, Biological Markers and Other Evaluation Tools", The Journal of Nutrition, Health & Aging, vol. 13, Issue No. 8, 2009, pp. 724-728, XP055397396.
European Office Action for Appl No. 19 700 310.6-1118 dated Jan. 19, 2023.

\* cited by examiner

Muscle gene expression changes between sarcopenia and controls

Muscle gene expression changes between sarcopenia and controls

Serum Trigonelline / Anthranilic acid ratio correlation with muscle gene expression

B

Muscle gene expression changes between sarcopenia and controls of NAD biosynthesis genes NMNAT1:
Nicotinamide Nucleotide Adenylyltransferase 1

NAMPT:
Nicotinamide phosphoribosyltransferase

PNP:
Purine Nucleoside Phosphorylase

NAD+ levels in muscle biopsies of control and sarcopenic participants.

METHODS TO PREDICT RISK OF AND TO STRATIFY SARCOPENIA AND NAD DEFICIENCY

CROSS REFERENCE TO RELATED APPLICATIONS

The present application is a National Stage of International Application No. PCT/EP2019/050819, filed on Jan. 14, 2019, which claims priority to European Patent Application No. 18152186.5, filed on Jan. 17, 2018, and European Patent Application No. 18187656.6, filed Aug. 7, 2018, the entire contents of which are being incorporated herein by reference.

BACKGROUND TO THE INVENTION

Age-related loss of muscle mass and function is inevitable in all individuals; however its progression largely depends on genetic and environmental factors such as physical activity and nutritional intake.

Sarcopenia has been defined as the point where the age-related loss of muscle mass and function gets debilitating and impacts quality of life. In contrast, frailty is another classification of age-related physical function decline that features low muscle strength and functionality, but not muscle mass. Sarcopenia is defined clinically according to low muscle mass and function, using cutoffs which stratify the elderly population for individuals in a state of pathological mobility. Sarcopenia predicts future disability and mortality, and was assigned an official ICD-10 disease code in 2016 (Anker et al., 2016).

Sarcopenia is common in both men and women over the age of 65 with the worldwide prevalence estimated at 3-30% according to the operational definition implemented. Sarcopenia is associated with a number of adverse physical and metabolic outcomes including frailty, disability, obesity, diabetes and osteoporosis. As a consequence, there is a substantial health care cost attributable to sarcopenia. Although age, gender, size, heritability and physical activity are recognised adult influences, there remains considerable unexplained variation in muscle mass and strength among older individuals.

Sarcopenia is a multi-factorial syndrome which associates with pathophysiological changes such as impaired neuromuscular transition, altered excitation/contraction coupling, impaired regenerative capacity linked to stem cell exhaustion, defects of mitochondrial and energy metabolism in myofibers, and finally marbling of skeletal muscle with fat and fibrosis. The etiology of the syndrome is therefore complex and poorly understood, but low physical activity, hormonal decline in anabolic hormones (androgens, IGF-1) and malnutrition/nutritional deficiencies play an important role.

The MEMOSA (Multi-Ethnic Molecular Determinants of Human Sarcopenia) study was designed in order to determine the molecular and nutritional changes associated with sarcopenia in humans.

The inventors of the present application have discovered that Anthranilic acid and Trigonelline levels in the body, and the ratio of Trigonelline:Anthranilic Acid levels are indicative of sarcopenia or increased risk of developing sarcopenia in a subject.

BRIEF DESCRIPTION OF THE FIGURES

FIG. 4A Gene set enrichment analysis of sarcopenic vs control muscle and FIG. 4B GSEA enrichment plot for the oxidative phosphorylation gene set selected from FIG. 4A. RNA sequencing of human sarcopenic skeletal muscle reveals that mitochondrial dysfunction is the major transcriptional change during sarcopenia.

FIG. 5A Gene set enrichment analysis of sarcopenic vs control muscle and FIG. 5B GSEA enrichment plot for the oxidative phosphorylation gene set selected from FIG. 5A. Positive correlation of skeletal muscle mitochondrial function gene expression with serum levels of trigonelline.

FIG. 6A Gene set enrichment analysis of sarcopenic vs control muscle and FIG. 6B GSEA enrichment plot for the oxidative phosphorylation gene set selected from FIG. 6A. Negative correlation of skeletal muscle mitochondrial function gene expression with serum levels of anthranilic acid.

FIG. 7A Gene set enrichment analysis of sarcopenic vs control muscle and FIG. 7B GSEA enrichment plot for the oxidative phosphorylation gene set selected from FIG. 7A. Positive correlation of skeletal muscle mitochondrial function gene expression with serum level ratios of trigonelline:anthranilic acid.

DESCRIPTION OF THE INVENTION

Figure 1:
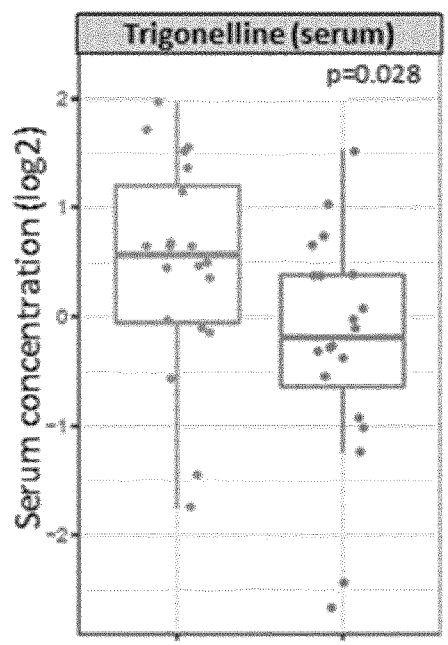
FIG. 1. Serum levels of trigonelline differ in sarcopenic patients and positively associate with lean muscle mass, grip strength and gait.
Figure 1:
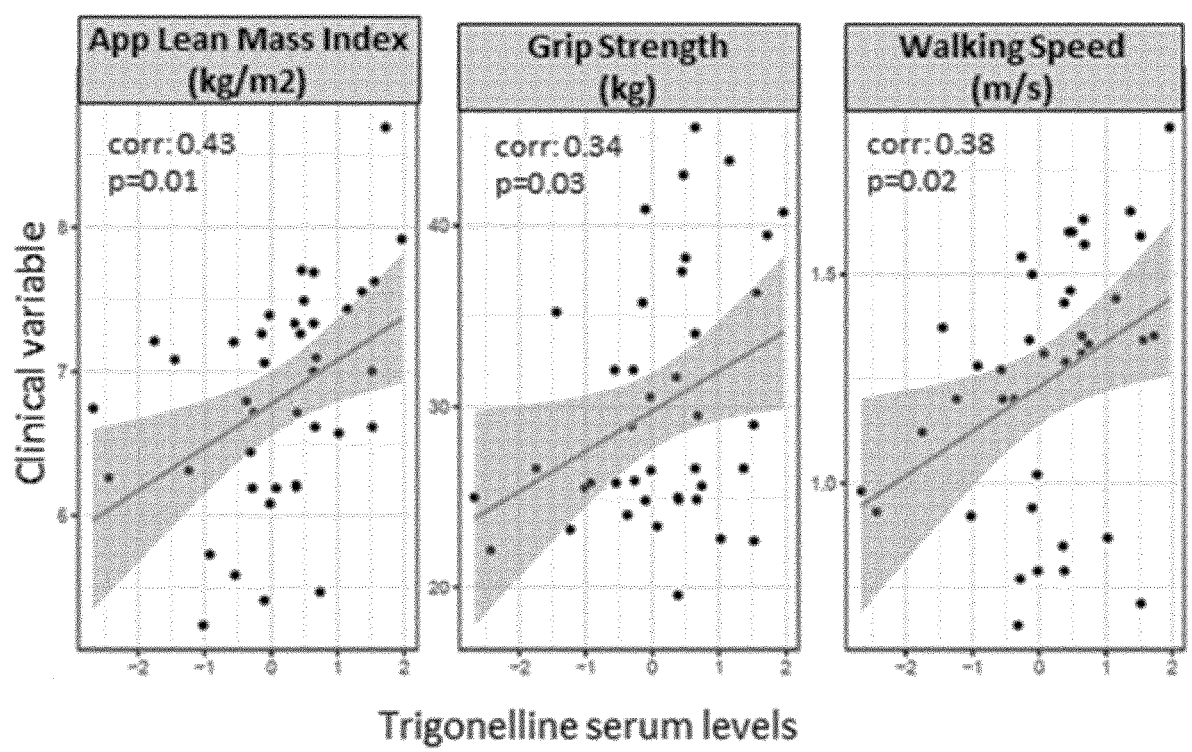

The invention relates to a method of determining if a subject has sarcopenia or has an increased risk of developing sarcopenia comprising:
(a) determining the level of Anthranilic acid in a sample obtained from the subject;
(b) comparing the level of Anthranilic acid in the sample to a reference value;
wherein an increased level of Anthranilic acid in the sample compared to the reference value is indicative of sarcopenia or risk of developing sarcopenia.

In one embodiment, the method further comprises:
(a) determining the level of Trigonelline in a sample obtained from the subject;
(b) comparing the level of Trigonelline in the sample to a reference value;
wherein a decreased level of Trigonelline in the sample compared to the reference value is indicative of sarcopenia or risk of developing sarcopenia in the subject.

The present invention also relates to a method for determining if a subject has sarcopenia or has an increased risk of developing saropenia comprising:
(a) determining the levels of Trigonelline and Anthranilic acid in a sample obtained from the subject;
(b) determining a ratio of Trigonelline:Anthranilic acid in the sample;
(c) comparing the ratio of Trigonelline:Anthranilic acid in the sample to a reference value;

wherein the ratio of Trigonelline:Anthranilic acid in the sample compared to the reference value is indicative of sarcopenia or risk of developing sarcopenia in the subject.

In one embodiment, a decrease in the Trigonelline:Anthranilic acid ratio in the sample from the subject compared to the reference value is indicative of sarcopenia or an increased risk of developing sarcopenia in the subject.

The present invention also relates to a method for determining if a subject has sarcopenia or has an increased risk of developing saropenia comprising:
(a) determining the levels of Trigonelline and Anthranilic acid in a sample obtained from the subject;
(b) determining a ratio of Anthranilic acid:Trigonelline in the sample;
(c) comparing the ratio of Anthranilic acid:Trigonelline in the sample to a reference value;
wherein the ratio of Anthranilic acid:Trigonelline in the sample compared to the reference value is indicative of sarcopenia or risk of developing sarcopenia in the subject.

In one embodiment, an increase in the Anthranilic acid:Trigonelline ratio in the sample from the subject compared to the reference value is indicative of sarcopenia or an increased risk of developing sarcopenia in the subject.

The present invention also relates to a method for determining if a subject has sarcopenia or has an increased risk of developing saropenia comprising:
(a) determining the levels of Trigonelline and Anthranilic acid in a sample obtained from the subject;
(b) determining the relative amounts or combinations of Anthranilic acid and Trigonelline in the sample;
(c) comparing the relative amounts or combinations of Anthranilic acid and Trigonelline in the sample to a reference value;
wherein the relative amounts or combinations of Anthranilic acid and Trigonelline in the sample compared to the reference value are indicative of sarcopenia or risk of developing sarcopenia in the subject.
and wherein the combination is defined as $n*f(A)+m*g(B)$ where A and B are the concentrations of Trigonelline and Anthranilic acid, $f()$ and $g()$ are representing mathematical transformations, n and m are numerical coefficients that can be positive or negative.

For example, the combination could be defined as $1*\log 2(A)+(-1)*\log 2(B)=\log 2(A/B)$ or $1*\log 2(A)-2 \log 2(B) = \log 2(A/(B)^2)$.

In one embodiment, the mathematical transformations comprise logarithmic transformations.

In one embodiment, an increase in the relative amount of Anthranilic acid to Trigonelline in the sample from the subject compared to the reference value is indicative of sarcopenia or an increased risk of developing sarcopenia in the subject.

In one embodiment, the invention relates to a method of determining if a subject has sarcopenia.

In one embodiment, the invention relates to a method of determining if a subject has an increased risk of developing sarcopenia.

Sarcopenia is characterized by one or more of low muscle mass, low muscle strength, and low physical performance. More preferably, sarcopenia is characterized by two or more of low muscle mass, low muscle strength, and low physical performance. Most preferably, sarcopenia is characterized by low muscle mass, low muscle strength, and low physical performance. These can all be measured by methods well known to the person skilled in the art.

Muscle mass can be measured by CT (computerised tomography), DXA (Dual-energy X-ray absorptiometry), MRI (Magnetic Resonance Imaging) or D3 creatine dilution methods.

Muscle strength can be measured by handgrip strength (for example, using hand held dynamometry) or knee extensor strength (for example, using quadriceps torque measurement).

Physical performance can be measured by gait speed, SPPB, 400 m walk test, time up and go test, or stair climbing test.

In one embodiment, the levels of Trigonelline and Anthranilic acid are determined by mass spectrometry. Preferably, the levels of Trigonelline and Anthranilic acid are determined by liquid chromatography followed by mass spectrometry.

In one embodiment, the subject is a human subject.
In one embodiment, the human subject is an older adult.
In one embodiment, the human subject is elderly.
In one embodiment, the subject is a companion animal, preferably a dog.

The invention relates to a method of determining if a subject has a muscle wasting condition or a muscle disease, or has an increased risk of developing a muscle wasting condition or a muscle disease comprising:
(a) determining the level of Anthranilic acid and/or Trigonelline in a sample obtained from the subject;
(b) comparing the level of Anthranilic acid and/or Trigonelline in the sample to a reference value;
wherein an increased level of Anthranilic acid in the sample compared to the reference value or a decreased level of Trigonelline in the sample compared to the reference value is indicative of a muscle wasting condition or a muscle disease, or risk of developing a muscle wasting condition or a muscle disease.

The present invention also relates to a method for determining if a subject has a muscle wasting condition or a muscle disease, or has an increased risk of developing a muscle wasting condition or a muscle disease comprising:
(a) determining the levels of Trigonelline and Anthranilic acid in a sample obtained from the subject;
(b) determining a ratio of Trigonelline:Anthranilic acid in the sample;
(c) comparing the ratio of Trigonelline:Anthranilic acid in the sample to a reference value;
wherein the ratio of Trigonelline:Anthranilic acid in the sample compared to the reference value is indicative of a muscle wasting condition or a muscle disease or an increased risk of developing a muscle wasting condition or a muscle disease in the subject.

In one embodiment, a decrease in the Trigonelline:Anthranilic acid ratio in the sample from the subject compared to the reference value is indicative of a muscle wasting condition or a muscle disease or an increased risk of developing a muscle wasting condition or a muscle disease in the subject.

The muscle wasting condition can be caused by disuse, immobilization, prolonged bed rest, ICU (intensive care unit) stay.

The muscle disease can be sarcopenia, cachexia (caused by chronic diseases like cancer, COPD, heart failure, kidney disease), genetic myopathies and dystrophies such as Duchenne muscular dystrophy, myotoxicity or rhabdomyolysis induced by drugs like corticosteroids or statins.

Preferably the muscle disease is sarcopenia.

The following embodiments relate to one or more of the above methods of the invention.

In one embodiment, the reference value is determined from a sample obtained from the same subject or from a group of subjects.

In one embodiment, the reference value is measured in a sample from the same subject.

In one embodiment, the reference value is measured in the same subject before a nutritional intervention, for example with a nutritional composition, and compared to the measurement after nutritional intervention.

In one embodiment, the reference value is measured in a sample from a group of subjects, for example a group of subjects of similar age.

In one embodiment, the subject is an older adult.

In one embodiment, the subject is elderly.

In one embodiment, the sample obtained from the subject is a plasma sample.

In one embodiment, the sample obtained from the subject is a serum sample.

In one embodiment, the sample obtained from the subject is a urine sample.

The present invention also relates to a nutritional composition for use in the treatment or prevention of sarcopenia in a subject.

In one embodiment, the subject is identified as having sarcopenia or is at increased risk of developing sarcopenia.

In one embodiment, the subject is identified as having sarcopenia or is at increased risk of developing sarcopenia by a method according to the invention.

In one embodiment, the nutritional composition comprises an NAD precursor. In one embodiment, the nutritional composition comprises trigonelline. In one embodiment, the nutritional composition comprises a precursor of trigonelline. In one embodiment, the nutrional composition comprises a derivative of trigonelline. Trigonelline is an alkaloid with chemical formula C7H7NO2 and CAS number 535-83-1.

In one embodiment, the subject is an older adult.

In one embodiment, the subject is elderly.

In one embodiment, the subject is identified as having sarcopenia by a method according to the invention, the nutritional composition comprises an NAD precursor, and the subject is elderly.

In one embodiment, the subject is identified as having sarcopenia by a method according to the invention, the nutritional composition comprises trigonelline, and the subject is elderly.

The present invention also relates to a method for treating or preventing sarcopenia in a subject.

In one embodiment, the subject is identified as having sarcopenia or is at increased risk of developing sarcopenia.

In one embodiment, the subject is identified as having sarcopenia or is identified as being at increased risk of developing sarcopenia by a method according to the invention.

In one embodiment, the method comprises modifying a lifestyle of the subject.

In one embodiment, modifying the lifestyle comprises physical activity, for example weight bearing, resistance or endurance exercise.

In one embodiment, modifying the lifestyle of the subject comprises a change in diet.

In one embodiment, a change in diet comprises administering at least one nutritional composition to the subject as part of a diet which treats or prevents sarcopenia.

In one embodiment, the nutritional composition comprises an NAD precursor.

In one embodiment, the subject is an older adult.

In one embodiment, the subject is elderly.

The present invention also relates to a method for predicting the responsiveness to nutritional composition of a subject having muscle wasting or a muscle disease, or having an increased risk of developing muscle wasting or a muscle disease.

In one embodiment, the nutritional composition comprises an NAD precursor, the subject is elderly, and the muscle disease is sarcopenia.

The present invention also relates to a method for predicting the responsiveness to nutritional composition of a subject having sarcopenia or having an increased risk of developing sarcopenia.

In one embodiment, the nutritional composition comprises an NAD precursor, and the subject is elderly.

In one embodiment, the method of the invention comprises:
(a) detecting the level of one or more biomarker(s) in a sample obtained from the subject;
(b) comparing the level of one or more biomarker(s) in the sample to a reference value;
(c) predicting the responsiveness of the subject to the nutritional composition based on the results of step (b).
wherein said one or more biomarker(s) is Anthranilic acid and/or Trigonelline.

The subject will be predicted to be responsive to a nutritional composition or nutritional intervention if the level of Anthranilic acid is increased in the sample compared to the reference value. The subject will be predicted to be responsive to a nutritional composition or nutritional intervention if the level of Trigonelline is decreased in the sample compared to the reference value.

In one embodiment, the biomarker is Anthranilic acid.

In one embodiment, the biomarker is Trigonelline.

In one embodiment, the biomarkers are a combination of Anthranilic acid and Trigonelline.

In one embodiment, the biomarkers are combination of Anthranilic acid, Trigonelline, 3-hydroxy-anthranilic acid, tryptophan, kynurenine, or their metabolites.

In one embodiment, the nutritional composition is Vitamin B3.

In one embodiment, the nutritional composition is an NAD precursor, for example nicotinamide riboside, nicotinamide mononucleotide, and nicotinamide.

In one embodiment, the nutritional composition is tryptophan, kynurenine and their metabolites.

In one embodiment, the nutritional composition is Trigonelline.

In one embodiment, the nutritional composition is derived from coffee, for example a coffee bean extract or coffee beverage. In one embodiment, said coffee extract comprises one or more of caffeic acid, trigonelline, quinolinic acid, and precursors of quinolinic acid.

Subject

The term "subject" means any animal, including humans and companion animals. Generally, the subject is a human or an avian, bovine, canine, equine, feline, hircine, murine, ovine or porcine animal. The subject can be a horse or a companion animal, for example a cat or a dog. Preferably, the subject is a human. The term "elderly" in the context of a human means an age from birth of at least 60 years, more preferably above 64 years, and most preferably above 68 years. The term "older adult" in the context of a human means an age from birth of at least 45 years, preferably above 50 years, more preferably above 55 years, and includes elderly subjects.

Sarcopenia

Sarcopenia can be characterized by one or more of low muscle mass, low muscle strength and low physical performance.

Sarcopenia can be diagnosed in a subject based on the definition of the AWGSOP (Asian Working Group for Sarcopenia in Older People), for example as described in Chen et al., 2014. Low muscle mass can generally be based on low appendicular lean mass normalized to height square (ALM index), particularly ALM index less than 7.00 kg/m$^2$ for men and 5.40 kg/m$^2$ for women. Low physical performance can generally be based on gait speed, particularly gait speed of <0.8 m/sec. Low muscle strength can generally be based on low hand grip strength, particularly hand grip strength less than 26 kg in men and less than 18 kg in women.

Sarcopenia can be diagnosed in a subject based on the definition of the EWGSOP (European Working Group for Sarcopenia in Older People), for example as described in Cruz-Jentoft et al., 2010. Low muscle mass can generally be based on low appendicular lean mass normalized to height square (ALM index), particularly ALM index less than 7.23 kg/m$^2$ for men and 5.67 kg/m$^2$ for women. Low physical performance can generally be based on gait speed, particularly gait speed of <0.8 m/sec. Low muscle strength can generally be based on low hand grip strength, particularly hand grip strength less than 30 kg in men and less than 20 kg in women.

Sarcopenia can be diagnosed in a subject based on the definition of the Foundation for the National Institutes of Health (FNIH), for example as described in Studenski et al., 2014. Low muscle mass can generally be based on low appendicular lean mass (ALM) normalized to body mass index (BMI; kg/m2), particularly ALM to BMI less than 0.789 for men and 0.512 for women. Low physical performance can generally be based on gait speed, particularly gait speed of <0.8 m/sec. Low muscle strength can generally be based on low hand grip strength, particularly hand grip strength less than 26 kg in men and less than 16 kg in women. Low muscle strength can also generally be based on low hand grip strength to body mass index, particularly hand grip strength to body mass index less than 1.00 in men and less than 0.56 in women.

The D3-creatine dilution method is another approach to measure muscle mass. This method is becoming more widely accepted as a robust standard and potentially a future alternative to DXA. The D3-creatine dilution method has been described previously in Clark et al. (2014) and Stimpson et al. (2013).

The present method involves determining the levels of Trigonelline, Anthranilic acid and/or the ratio of their levels in a sample obtained from a subject. This may be referred to as the 'test sample'. Thus the present method is typically practiced outside of the human or animal body, e.g. on a body fluid sample that was previously obtained from the subject to be tested.

The sample may, for example, be a serum, plasma or urine sample. The sample can be derived from blood, i.e. the sample comprises whole blood or a blood fraction. The sample may comprise blood plasma or serum. Preferably, the sample is a serum sample.

Techniques for collecting blood samples and separating blood fractions are well known in the art. For instance, vena blood samples can be collected from patients using a needle and deposited into plastic tubes. The collection tubes may, for example, contain spray-coated silica and a polymer gel for serum separation. Serum can be separated by centrifugation at 1300 RCF for 10 min at room temperature and stored in small plastic tubes at −80° C.

Comparison to Reference Value

The present method involves a comparison of Anthranilic acid and Trigonelline levels to reference value levels of Anthranilic acid and Trigonelline. The term reference value is synonymous with 'control value' and broadly includes data that the skilled person would use to facilitate the accurate interpretation of technical data.

The levels of Anthranilic acid, the levels of Trigonelline, and/or the ratio of Trigonelline:Anthranilic acid levels in a sample from a subject may be compared to that of the same subject or that of one or more cohorts (populations/groups) of control subjects.

Reference values may be established by assaying samples from the same subject, for example by assay of repeat samples. Reference values may also be established by assaying samples from individuals in the general population or the selected population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is incorporated herein by reference.

Reference values may be established by assaying at least 1 individual, more preferably at least 5 individuals, more preferably at least 10 individuals, more preferably at least 15 individuals, most preferably at least 20 individuals. All or a substantial number of said individuals preferably do not have sarcopenia.

In is known in the art how to assign correct reference values as they will vary with gender, race, genetic heritage, health status or age, for example.

Nutritional Composition

A nutritional composition according to the invention may be a nutraceutical composition, functional food, functional nutrition product, medical food with regulatory status as drugs, medical nutrition product, or dietary supplement.

The term "nutraceutical" combines the words "nutrition" and "pharmaceutical". It is a food or food product that provides health and medical benefits, including the prevention and treatment of disease. A nutraceutical is a product isolated or purified from foods that is generally sold in medicinal forms not usually associated with food. A nutraceutical is demonstrated to have a physiological benefit or provide protection against chronic disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, nutraceutical compositions can be used as supplements to food and beverages and as pharmaceutical formulations for enteral or parenteral application which may be solid formulations, such as capsules or tablets, or liquid formulations, such as solutions or suspensions.

The nutritional composition according to the invention may comprise trigonelline, a precursor of trigonelline and/or a derivative of trigonelline. The precursor of trigonelline may be, for example, quinolinic acid, nicotinic acid, and/or nicotinamide.

Preferably, the nutritional composition according to the invention comprises an NAD precursor, for example nicotinamide riboside, nicotinamide mononucleotide, nicotinamide and/or nicotinic acid.

Nutritional compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Moreover, a multi-vitamin and mineral supplement may be added to nutritional compositions of the invention to obtain an adequate amount of an essential nutrient, which is missing in some diets. The multi-vitamin and mineral supplement may also be useful for disease prevention and protection against nutritional losses and deficiencies due to lifestyle patterns.

Nutritional compositions of the invention may be in any galenic form that is suitable for administering to the body, especially in any form that is conventional for oral administration, e.g. in solid forms such as (additives/supplements for) food or feed, food or feed premix, fortified food or feed, tablets, pills, granules, dragees, capsules and effervescent formulations, such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The nutritional compositions may be in the form of controlled (delayed) release formulations.

Nutritional compositions may include beverages. The term "beverages" encompasses non-alcoholic and alcoholic drinks as well as liquid preparations to be added to drinking water and liquid food. Non-alcoholic drinks are e.g. soft drinks, sports drinks, fruit juices, teas and milk-based drinks Liquid foods may include soups and dairy products. The nutraceutical composition comprising the compound of the invention may be added to a soft drink, an energy bar, or a candy.

If the nutritional composition is a nutraceutical formulation the composition further contains pharmaceutically acceptable excipients, diluents or adjuvants then standard techniques may be used for their formulation, as e.g. disclosed in Remington's Pharmaceutical Sciences, 20th edition Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

"Functional food", "functional nutrition product", "medical food" and "medical nutrition product" relate to any healthy food claimed to have a health-promoting or disease-preventing property beyond the basic function of supplying nutrients. The general category of functional foods includes processed food or foods fortified with health-promoting additives, like "vitamin-enriched" products.

A dietary supplement, also known as food supplement or nutritional supplement, is a preparation intended to supplement the diet and provide nutrients, such as vitamins, minerals, fiber, fatty acids, or amino acids, that may be missing or may not be consumed in sufficient quantities in a person's diet. Some countries define dietary supplements as foods, while in others they are defined as drugs or natural health products. Supplements containing vitamins or dietary minerals are included as a category of food in the Codex *Alimentarius*, a collection of internationally recognized standards, codes of practice, guidelines and other recommendations relating to foods, food production and food safety. These texts are drawn up by the Codex *Alimentarius* Commission, an organization that is sponsored by the Food and Agriculture Organization of the United Nations (FAO) and the World Health Organization (WHO).

Prevention or Treatment of Disease

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. All of these terms also refer to the maintenance and/or promotion of health in a subject not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The invention will now be further described by way of Examples, which are meant to serve to assist one of ordinary skill in the art in carrying out the invention and are not intended in any way to limit the scope of the invention.

EXAMPLES

Example 1

Metabolite Measurements in Serum

Twenty male participants of predominantly Chinese descent aged 65-79 years and 20 control subjects of the same age group without a diagnosis of sarcopenia were recruited from 2 studies on healthy community-dwelling older men in Singapore (Singapore Sarcopenia Group and Ageing in a Community Environment Study [ACES]). Sarcopenia was diagnosed using the definition of the Asian Working Group for Sarcopenia in Older People (Chen et al., 2014), following the standardized operational definition of sarcopenia (Cruz-Jentoft et al., 2010).

The National Healthcare Group Domain-Specific Research Board (NHG DSRB) approved the study, reference number 2014/01304 and each participant gave written informed consent. Weight and height was measured in the nearest 0.1 kg or 1cm. Total lean mass was measured through dual energy X-ray absorptiometry (DXA) scanning (APEX Software version 4.0.1, Discovery Wi DXA system). A standardised protocol was used to measure isometric hand grip with Jamar hand-held dynamometer and the mean of 3 attempts from the dominant hand was used as the final measure. Physical performance was assessed by measuring gait speed in a 6 meter customary-paced walk test. The diagnosis of sarcopenia was based on AWGSOP definition that was defined as the total appendicular lean mass normalized for height less than 7.00 kg/m2, evidence of either low physical performance based on gait speed of <0.8 m/sec OR low muscle strength based on hand grip <26 kg. Anthropometric parameters were the following in the control and sarcopenic groups:

|  | Control (n = 20) Mean +/− SD | Sarcopenic (n = 20) Mean +/− SD | p-value |
|---|---|---|---|
| Height (m) | 1.67 +/− 0.06 | 1.63 +/− 0.07 | N.S. |
| Weight (kg) | 63.08 +/− 6.06 | 57.60 +/− 5.45 | 0.005 |
| Body mass index (kg/m$^2$) | 22.70 +/− 1.01 | 21.47 +/− 1.54 | 0.005 |
| Age (years) | 70.20 +/− 4.10 | 72.75 +/− 4.18 | N.S. |
| Total Lean body mass (by dual energy X-ray absorptiometry) (kg) | 44.53 +/− 3.86 | 38.36 +/− 3.01 | 2.18E−06 |
| Fat Mass (by dual energy X-ray absorptiometry) (kg) | 15.39 +/− 3.67 | 15.73 +/− 4.02 | N.S. |
| Appendicular Lean Mass index (kg/m$^2$) | 7.42 +/− 0.39 | 6.20 +/− 0.48 | 1.44E−08 |
| Grip strength (kg) | 35.11 +/− 5.93 | 24.91 +/− 2.56 | 2.02E−08 |
| Gait speed (m/s) | 1.40 +/− 0.23 | 1.09 +/− 0.29 | 0.0006 |

Fasting blood samples were taken from the antecubital fossa using vacutainer tubes and an indwelling 20 ga butterfly. Blood was centrifuged at 4° C. 3000 rpm for 10 minutes and the serum was aliquoted and frozen at −80° C. until further analysis. Anthranilic acid and trigonelline levels in serum were measured by liquid chromatography followed by mass spectrometry (LC-MS/MS) at BEVITAL laboratories (Bergen, Norway). Semi-open muscle biopsies of the vastus lateralis muscle were collected using a BioPince™ (Angiotech) 16G full core biopsy needle with 3 adjustable stroke lengths (13 mm, 23 mm, 33 mm) from the 20 male participants and 20 aged matched controls, and snap frozen in liquid nitrogen and stored at −80° C. until further analysis.

Differences in the serum levels of trigonelline, anthranilic acid and their ratio (trigonelline:anthranilic acid) between sarcopenic cases and controls were tested using Wilcoxon test and Student t-test after log 2 transformation. The inventors looked at the association between these analytes and the continuous clinical variables used for the characterization of sarcopenia (appendicular lean muscle mass index (ALMi; kg/m$^2$), grip strength and walking speed) applying both Spearman rank correlation and Pearson correlation after log 2 transformation of the serum concentration of the analytes.

Figure 2:
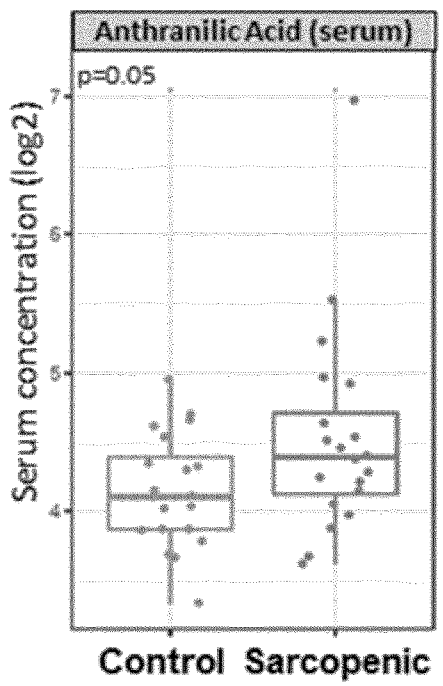
FIG. 2. Serum levels of anthranilic acid differ in sarcopenic patients and negatively associate with lean muscle mass, grip strength and gait.
Figure 2:
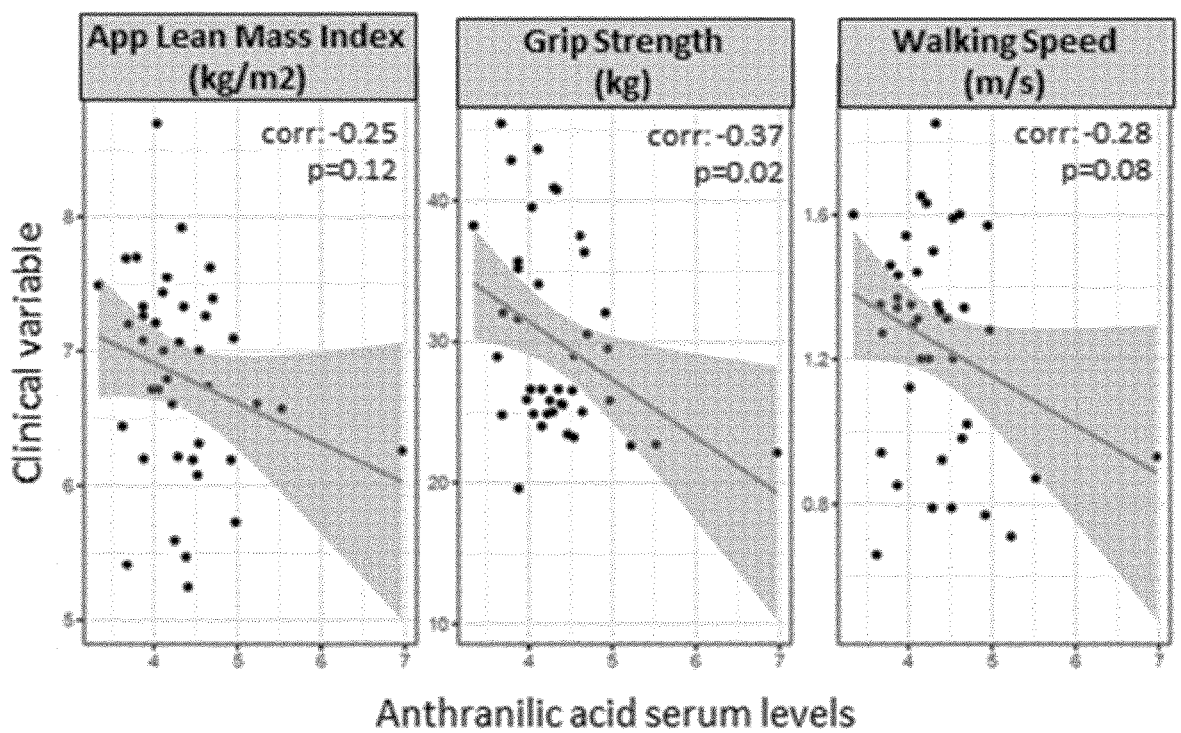
Figure 3:
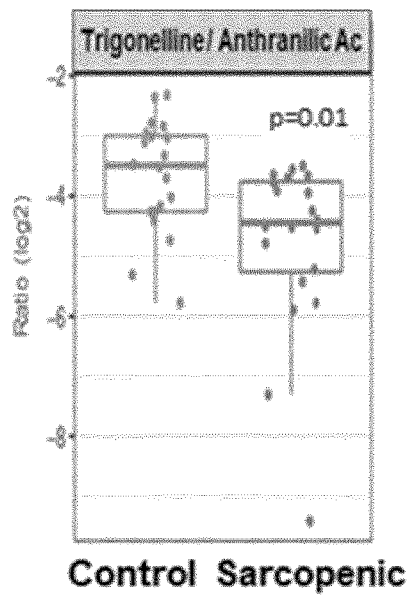
FIG. 3. Serum levels of trigonelline:anthranilic acid ratio differ in sarcopenic patients and positively associate with lean muscle mass, grip strength and gait.
Figure 3:
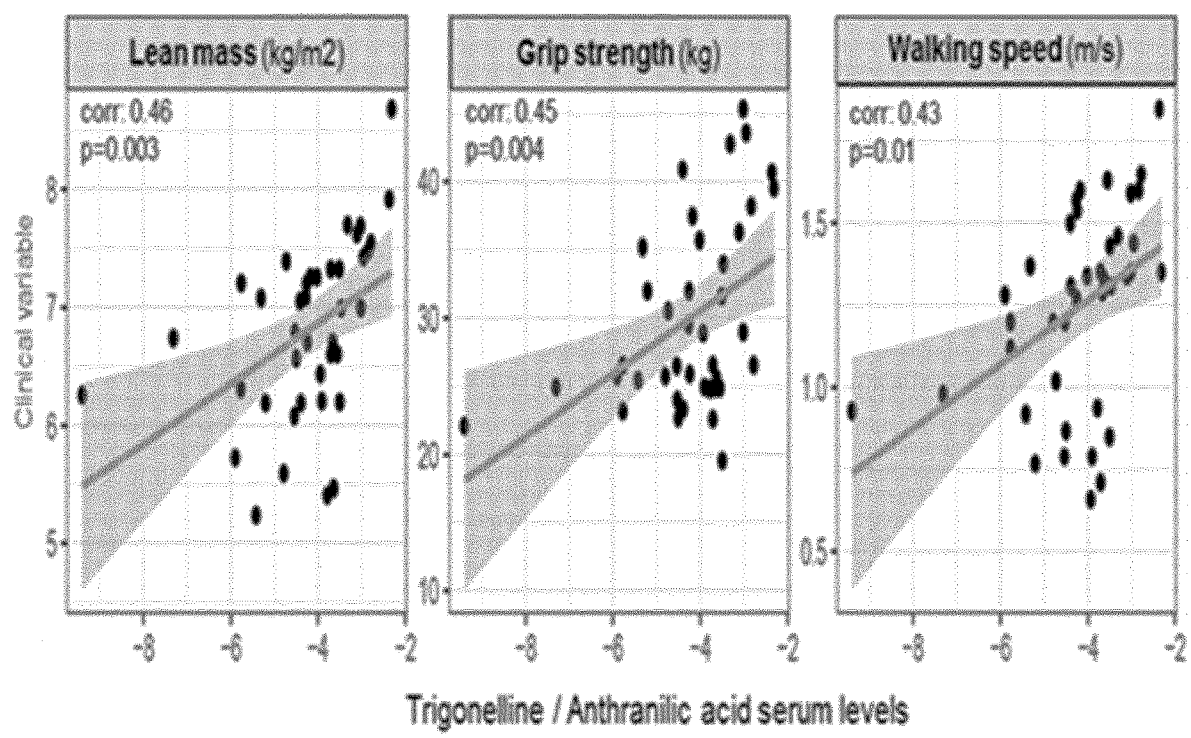

FIGS. 1 to 3 show that serum levels of trigonelline, anthranilic acid and trigonelline:anthranilic acid ratio differ in sarcopenic patients and associate with lean muscle mass, grip strength and gait. Levels of trigonelline (FIG. 1), anthranilic acid (FIG. 2) and trigonelline/anthranilic acid ratio (FIG. 3) were measured in the serum in a human cohort of 20 sarcopenic patients and 20 age-matched control, all aged 65 and above. The left panels represent the log 2 values of the analytes in serum of sarcopenic vs control patients. The right panels represent the association of analytes in serum with appendicular lean body mass index (ALMi) measured by DXA as surrogate for muscle mass, hand grip strength and gait speed. The orange line shows the fitted regression line of the clinical variables on the analytes and the gray area shows the 95% confidence intervals of the fitted model. P-values reported were computed with a Student T statistics (case control) or Pearson correlation (correlation analysis) on Log 2-transformed values.

Example 2

Muscle Gene Expression Analysis

For muscle gene expression analysis, total RNA was extracted from muscle biopsies using a Qiagen kit according to the manufacturer's instruction. RNA quantity was measured with Ribogreen (Life Technologies) and RNA quality was checked using the Standard Sensitivity RNA Analysis Kit on a Fragment Analyzer (Advanced Analytical Technologies). All RNA samples were homogeneous and passed quality control with 260/280 nm ratio >1.8 and RIN scores >7. For RNA sequencing, 250 ng of total RNA from each sample was employed as starting material for library preparation and the Ribo-Zero magnetic Kit (Illumina) was used to remove ribosomal RNA. Sequencing libraries were prepared using the TruSeq Stranded RNA HT with Ribo-Zero Gold Kit (Illumina) followed by 13 cycles of PCR amplification step with the KAPA HiFi HotStart ReadyMix (Kapa BioSystems). Libraries were quantified with Picogreen (Life Technologies) and size pattern was controlled with the DNA High Sensitivity Reagent kit on a LabChip GX (Perkin Elmer). Libraries were then pooled at an equimolar ratio and clustered at a concentration of 7 pmol on paired-end sequencing flow cell (Illumina). Sequencing was performed for 2×101 cycles on a HiSeq 2500 (Illumina) with V3 chemistry. The generated data were demultiplexed using Casava. Reads were aligned to the human genome (hs_GRCh38.p2) using STAR (Dobin et al., 2013), and the number of reads mapped within genes was quantified by HTSeq (Anders et al., 2015) (version HTSeq-0.6.1p1, mode union, strand reverse, quality alignment greater than 10). Samples had a sequencing depth of 75-104 million reads per sample, of which 34-77 million reads where uniquely mapped.

Differentially expressed genes between control and sarcopenic samples were defined by using limma package (Smyth, 2004). Briefly, after removing genes with a mean expression lower than 20 reads, data were normalized by the trimmed mean of M-values (TMM) method as implemented in the edgeR function calcNormFactors (Robinson et al., 2010), and the voomWithQualityWeights function was applied to model the mean-variance relationship and estimate the sample-specific quality weights (Liu et al., 2015). P-values were corrected for multiple testing using the Benjamini-Hoechberg method. The same procedure was applied when characterizing the associations between gene expression and the continuous or categorical parameters (ALMi, grip strength and walking speed) used to define sarcopenia. Gene set enrichment analysis was performed using CAMERA (Wu and Smyth, 2012), a competitive gene set test querying whether a set of genes annotated in the Molecular Signatures Database (MSigDB) (Subramanian et al., 2005) is enriched in differentially expressed genes. The MSigDB v5.2 collections H (hallmark gene sets), C2 (curated gene sets) and C5 (GO gene sets) were used to performed pathway analysis.

Figure 4A:
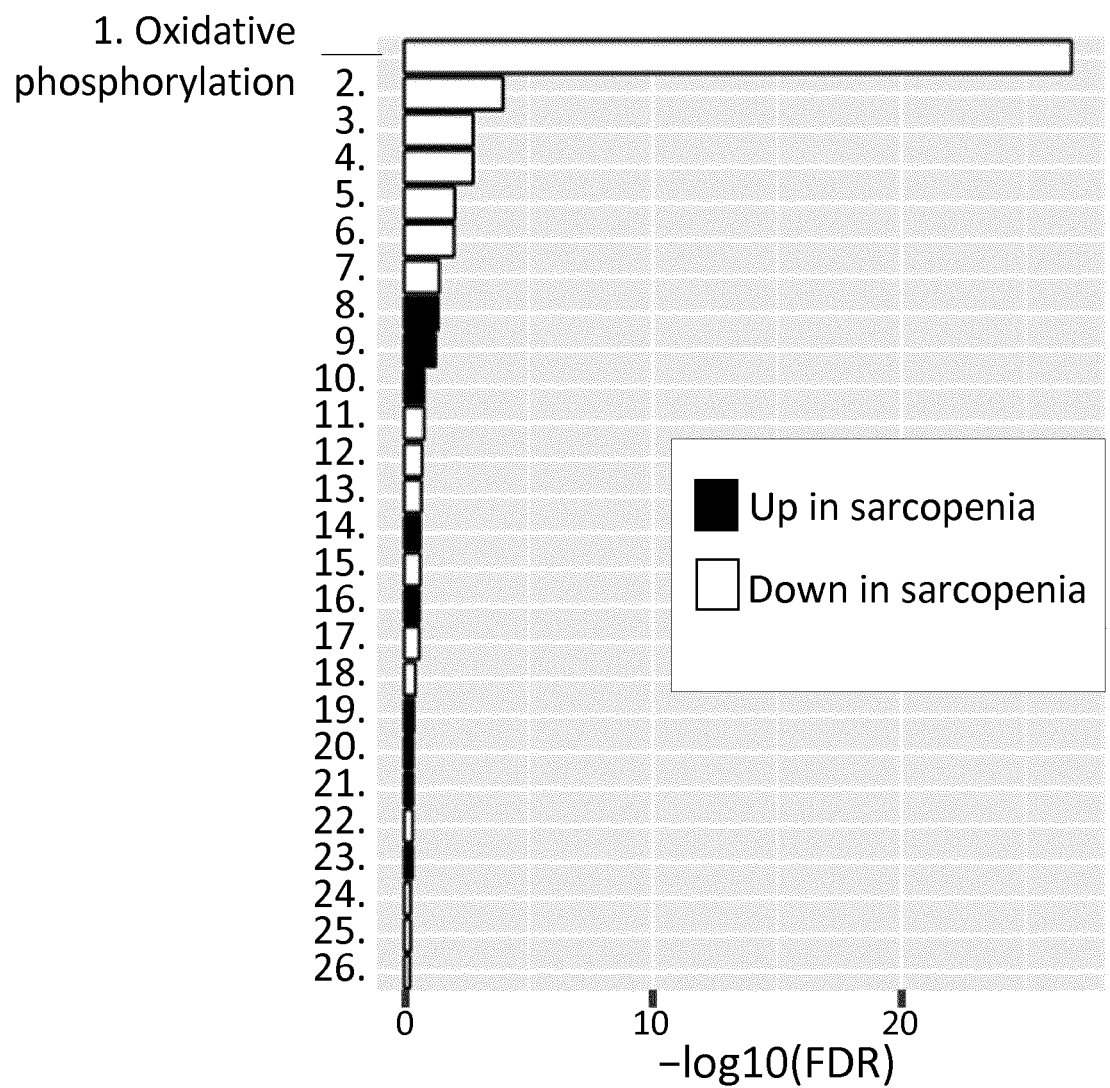
FIGS. 4A and 4B.
Figure 4B:
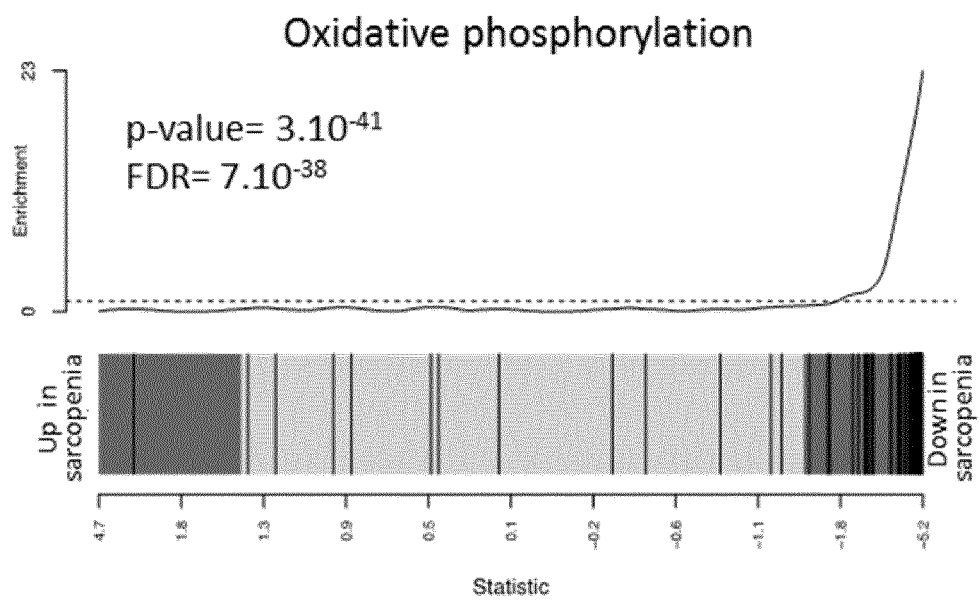

In FIG. 4, RNA sequencing of human sarcopenic skeletal muscle reveals that mitochondrial dysfunction is the major transcriptional change during sarcopenia. (A) Gene set enrichment analysis of sarcopenic vs control muscle using CAMERA and the hallmark gene set collection from MSigDB. Red bars represent gene sets enriched in sarcopenic muscle, and blue bars represent gene sets repressed in sarcopenic muscle. Gene sets are ordered according to the significance of their enrichment. (B) GSEA enrichment plot for the oxidative phosphorylation gene set selected from A.

Spearman rank correlation between TMM normalized muscle gene expression and each serum analyte of interest (trigonelline, anthranilic acid and trigonelline:anthranilic acid ratio) was computed and the Spearman rank correlation was used to perform gene set enrichment analysis using the biological hallmark gene set collection.

Key to FIG. 4A: 1. OXIDATIVE_PHOSPHORYLATION, 2. FATTY_ACID_METABOLISM, 3. MYC_TARGETS_V1, 4. ALLOGRAFT_REJECTION, 5. MTORC1_SIGNALING, 6. PEROXISOME, 7. ADIPOGENESIS, 8. EPITHELIAL_MESENCHYMAL_TRANSITION, 9. APICAL_JUNCTION, 10. G2M_CHECKPOINT, 11. BILE_ACID_METABOLISM, 12. UNFOLDED_PROTEIN_RESPONSE, 13. REACTIVE_OXYGEN_SPECIES_PATHWAY, 14. MITOTIC_SPINDLE, 15. UV_RESPONSE_UP, 16. UV_RESPONSE_DN, 17. PI3K_AKT_MTOR_SIGNALING, 18. MYC_TARGETS_V2, 19. KRAS_SIGNALING_DN, 20. HEDGEHOG_SIGNALING, 21. E2F_TARGETS, 22. INTERFERON_GAMMA_RESPONSE, 23. APICAL_SURFACE, 24. TGF_BETA_SIGNALING, 25. PROTEIN_SECRETION, 26. IL2_STAT5_SIGNALING.

Figure 5A:
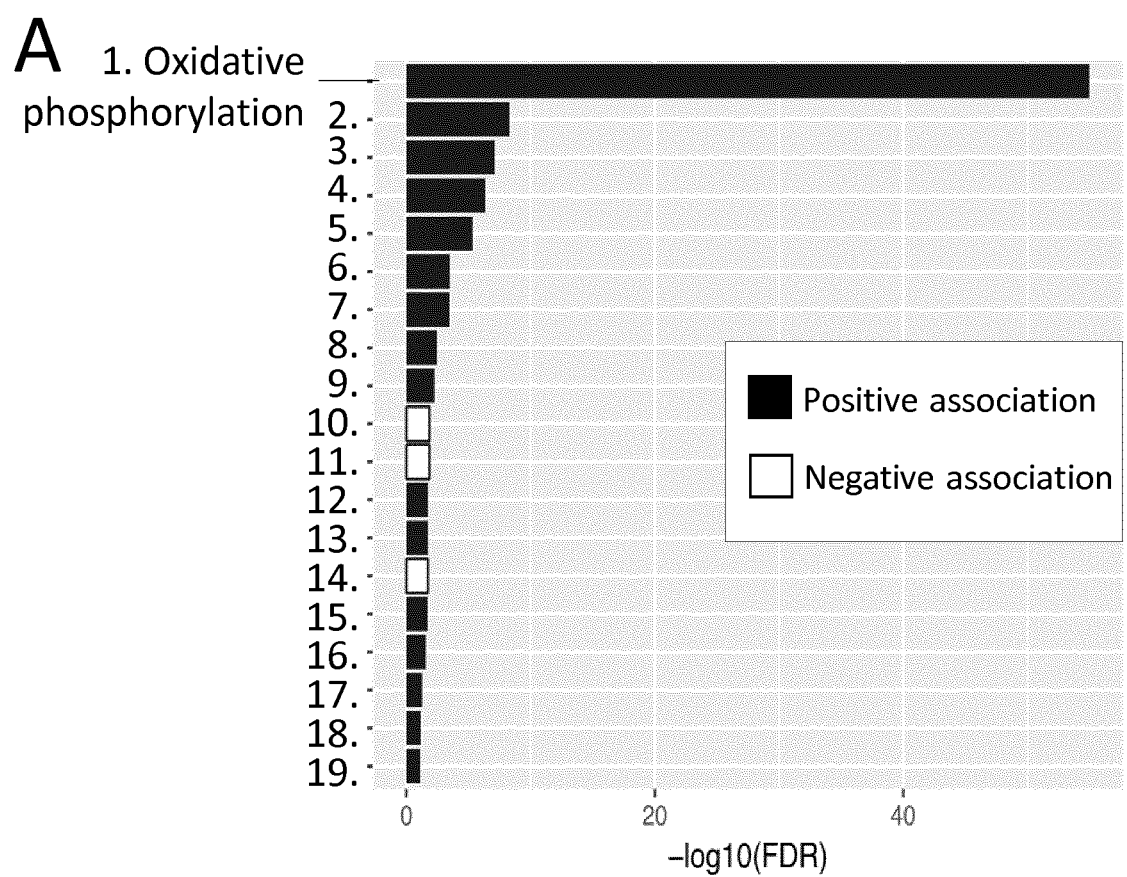
FIGS. 5A and 5B.
Figure 5B:
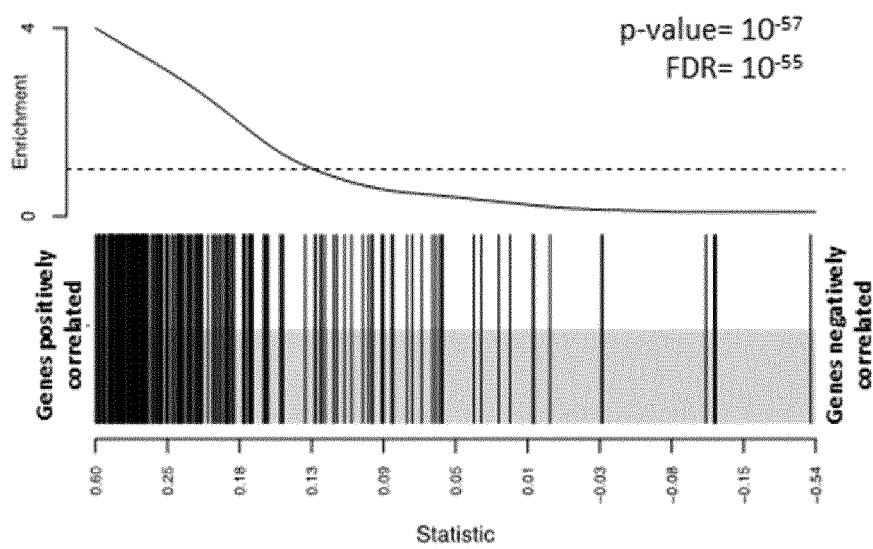
Figure 6A:
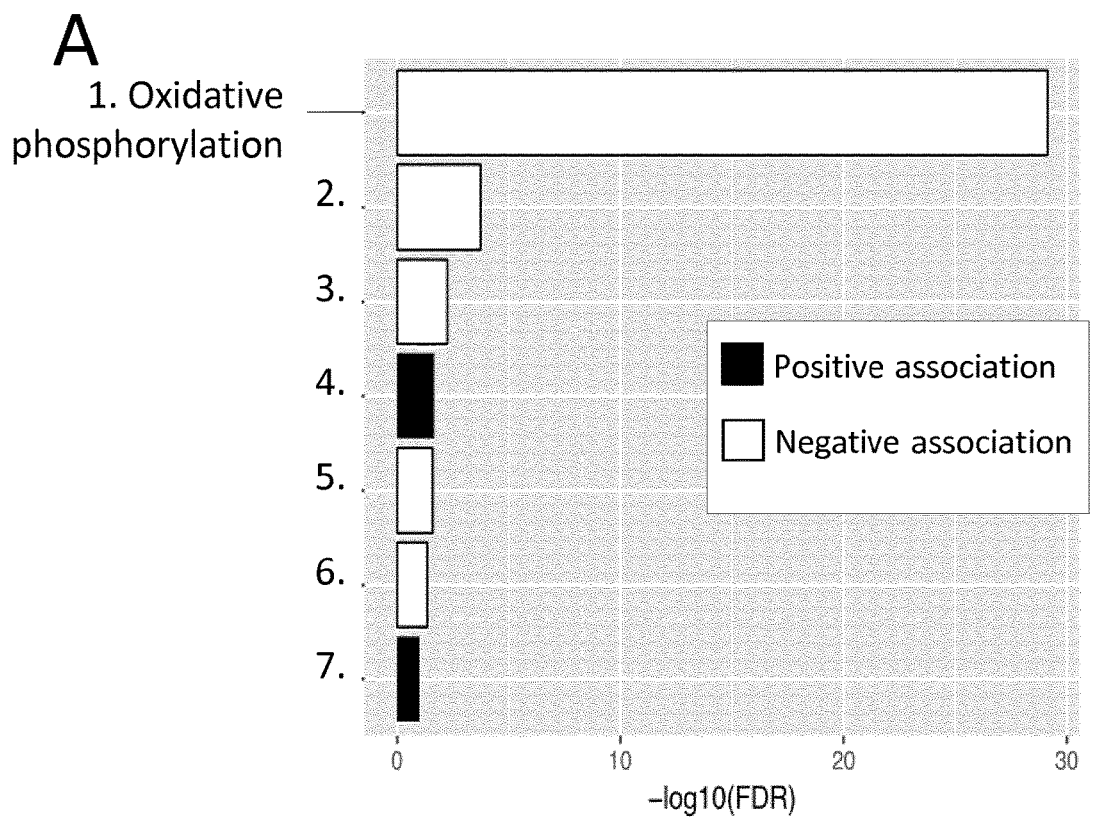
FIGS. 6A and 6B.
Figure 6B:
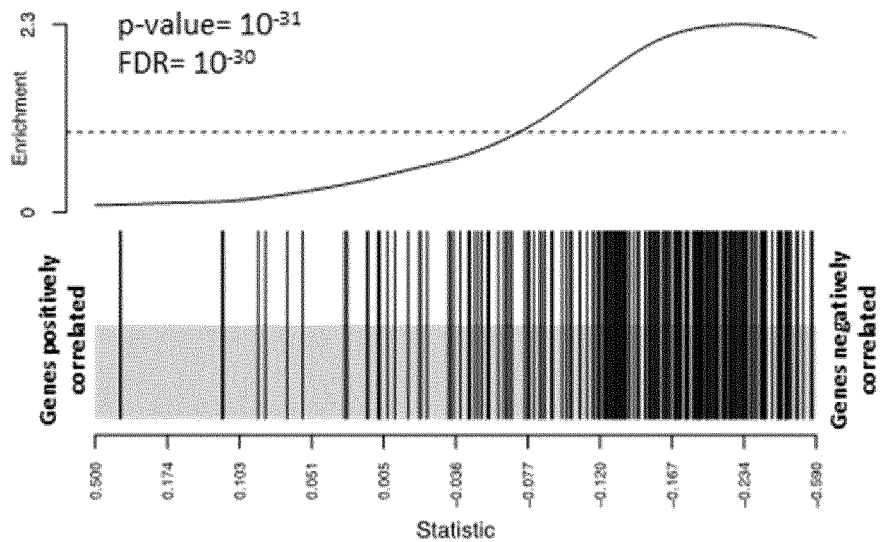
Figure 7A:
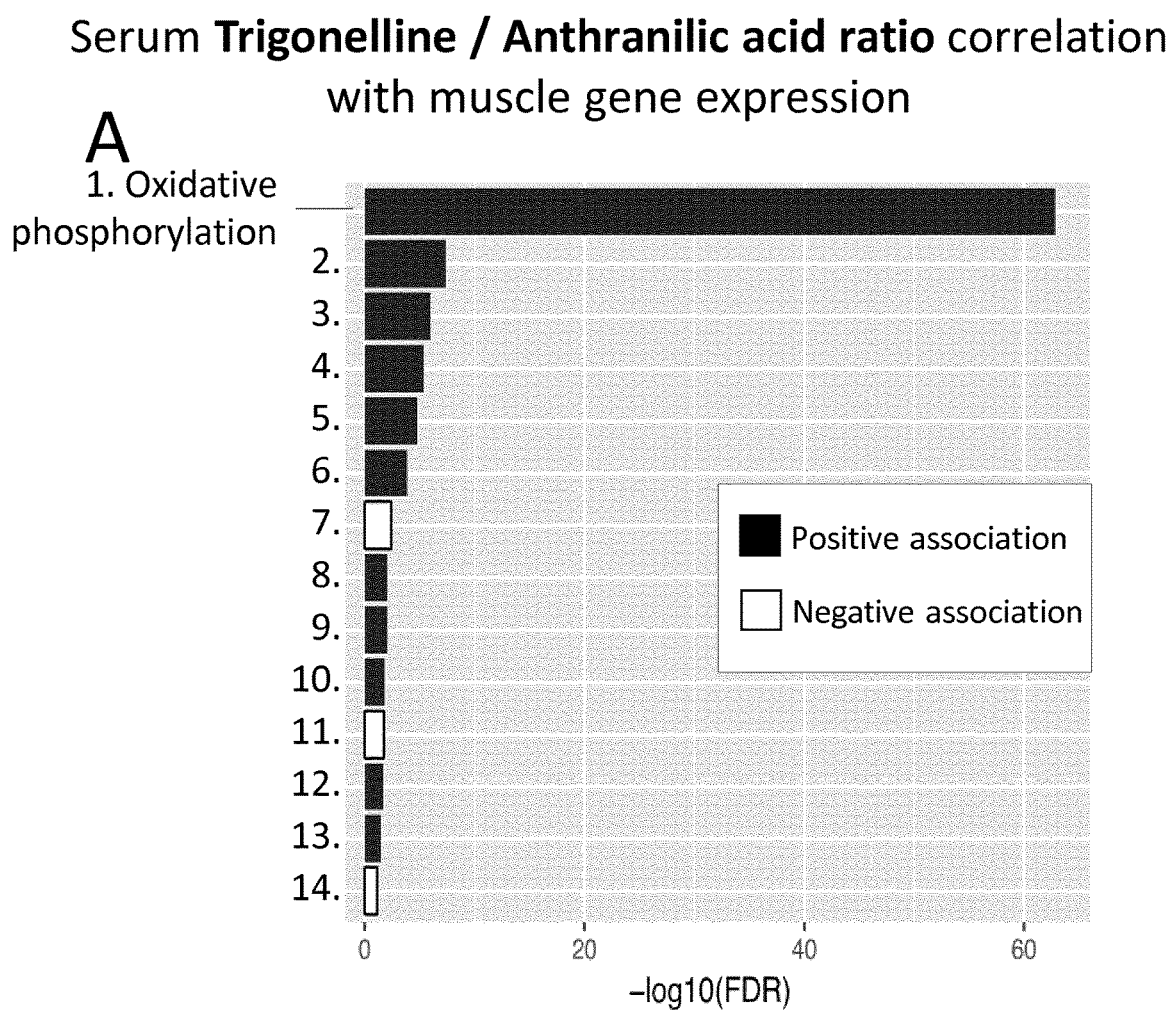
FIGS. 7A and 7B.
Figure 7B:
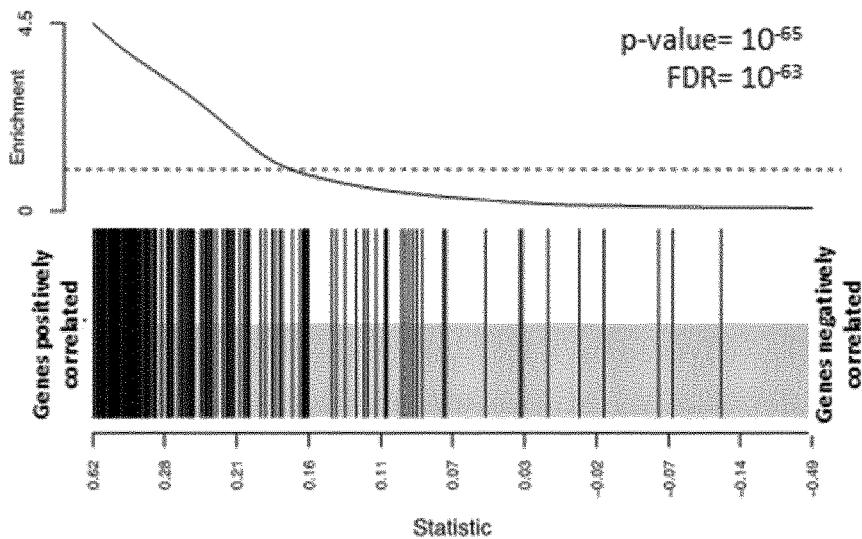

FIGS. 5 to 7 shows the correlation of skeletal muscle gene expression with serum levels of trigonelline, anthranilic acid and trigonelline:anthranilic acid ratio. Gene set enrichment analysis (GSEA) of muscle gene expression correlating with serum levels of trigonelline (FIG. 5), anthranilic acid (FIG. 6) and trigonelline/anthranilic acid ratio (FIG. 7). GSEA was performed using mean-rank gene set test and the biological hallmark gene set collection from MSigDB. Red bars represent gene sets whose expression in skeletal muscle positively correlates with serum levels of the analyte, and blue bars represent gene sets whose expression in skeletal muscle negatively correlates with serum levels of the analyte. Gene sets are ordered according to the significance of their enrichment and only gene sets with an FDR <1% are represented. Left panels represent the GSEA enrichment plot for the oxidative phosphorylation gene set.

Key to FIG. 5A: 1. OXIDATIVE_PHOSPHORYLATION, 2. MTORC1_SIGNALING, 3. PROTEIN_SECRETION, 4. ADIPOGENESIS, 5. FATTY_ACID_METABOLISM, 6. MYC_TARGETS_V1, 7. PEROXISOME, 8. DNA_REPAIR, 9. GLYCOLYSIS, 10. MITOTIC_SPINDLE, 11. MYOGENESIS, 12. INTERFERON_GAMMA_RESPONSE, 13. PI3K_AKT_MTOR_SIGNALING, 14. WNT_BETA_CATENIN_SIGNALING, 15. INTERFERON_ALPHA_RESPONSE, 16. ALLOGRAFT_REJECTION, 17. BILE_ACID_METABOLISM, 18. ANDROGEN_RESPONSE, 19. CHOLESTEROL_HOMEOSTASIS

Key to FIG. 6A: 1. OXIDATIVE_PHOSPHORYLATION, 2. FATTY_ACID_METABOLISM, 3. ADIPOGENESIS, 4. G2_M_CHECKPOINT, 5. BILE_ACID_METABOLISM, 6. PEROXISOME, 7. MYOGENESIS

Key to FIG. 7A: 1. OXIDATIVE_PHOSPHORYLATION, 2. FATTY_ACID_METABOLISM, 3. ADIPOGENESIS, 4. MTORC1_SIGNALING, 5. PEROXISOME, 6. PROTEIN_SECRETION, 7. MYOGENESIS, 8. G2M_CHECKPOINT, 9. MYC_TARGETS_V1, 10. BILE_ACID_METABOLISM, 11. DNA_REPAIR, 12. CHOLESTEROL_HOMEOSTASIS, 13. KRAS_SIGNALING_DN, 14. GLYCOLYSIS

Figure 8:
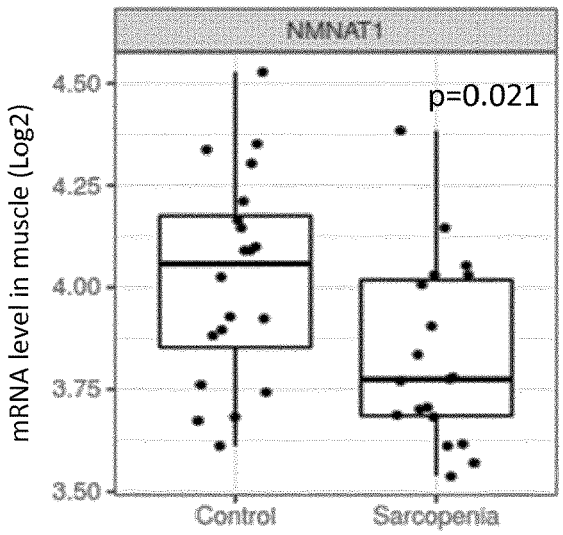
FIG. 8. Human sarcopenic muscle has lower expression of genes such as NMAT1, NAMPT and PNP.
Figure 8:
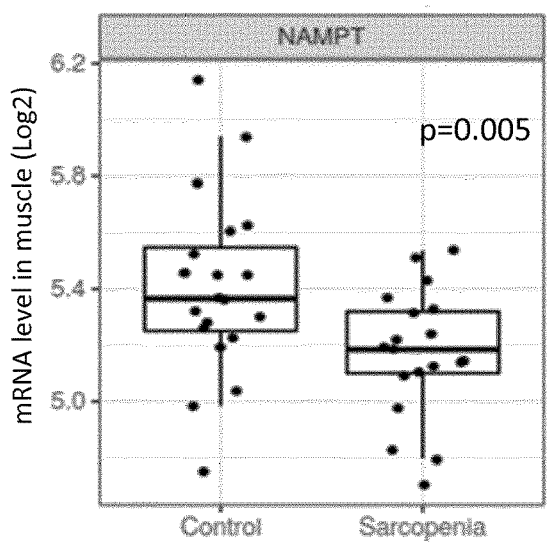
Figure 8:
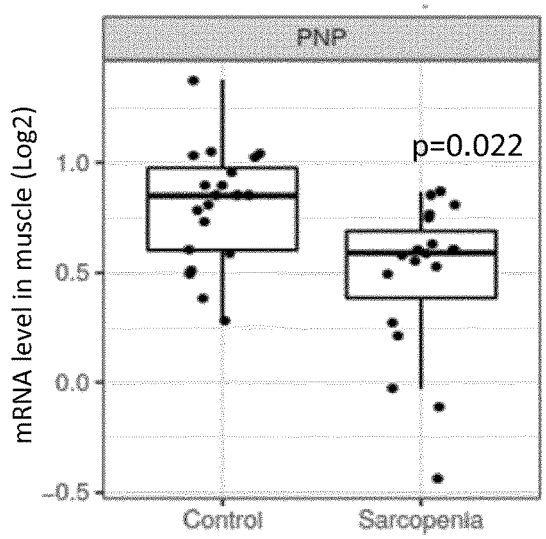

FIG. 8, shows that human sarcopenic muscle has lower expression of genes such as NMAT1, NAMPT and PNP, which control the biosynthesis of NAD from NAD precursors or from the diet and NAD salvage. Gene expression was measured in muscle by high coverage RNA sequencing. NMNAT: Nicotinamide Nucleotide Adenylyltransferase 1; NAMPT: Nicotinamide phosphoribosyltransferase; PNP: Purine Nucleoside Phosphorylase).

Example 3

Measurement of NAD+ Levels in Muscle Biopsies

In order to determine whether NAD levels could be an upstream trigger to the mitochondrial signature of sarcopenic muscle, NAD was measured in aged human muscle biopsy material. NAD+ levels were measured in human muscle biopsies as described in Dall et al, 2018. Briefly, 5 mg muscle tissue from remaining biopsies was lysed in 200 µL 0.6M perchloric acid and the supernatant was diluted 250-fold in 100 mM Na2HPO4 pH 8.0. 100 µL of diluted sample was combined with 100 µL reaction mix (100 mM Na2HPO4 pH 8, 2% ethanol, 90U/mL alcohol dehydrogenase, 130 mU/mL diaphorase, 10 µM resazurin, 10 µM flavin mononucleotide, 10 mM nicotinamide), and the fluorescence increase (Ex 540 nm/Em 580) was measured over 10 min. NAD+ content was calculated from a standard curve and normalized to tissue weight.

Figure 9:
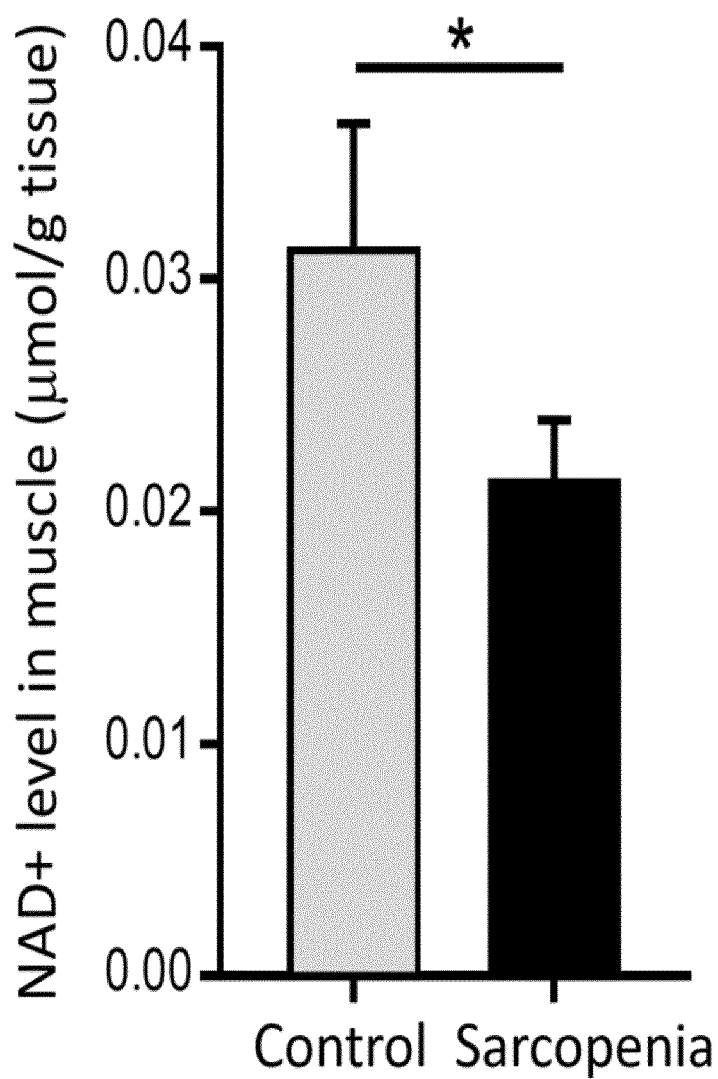
FIG. 9. NAD+ levels in muscle biopsies of control and sarcopenic participants.

FIG. 9 shows that there was a significant (32%) reduction of NAD levels in human skeletal muscle of aged sarcopenic patients. This major reduction of NAD+ levels in skeletal muscle from people with sarcopenia links for the first time low NAD+ levels to an age-related pathology in humans and constitutes the first demonstration of NAD deficiency in human skeletal muscle. Combined with preclinical efficacy of NAD precursors like NR and NMN on aged muscle in mice, this result will expand the clinical relevance of NAD biology in aging, as well as guide clinical translation for sarcopenia and age-related mobility deficits.

Example 4

Metabolite measurements in serum for a different ethnic group and including females.

Seventy participants of predominantly Caucasian origin, 52 females and 18 males, median 78 years (interquartile range 76, 81) were considered in this example.

These 70 participants were part of the Hertfordshire Sarcopenia Study (HSS), a sub study of the UK Hertfordshire Cohort Study (HCS) designed to investigate life course influences on muscle morphology, mass and strength in community-dwelling older people, or part of the extension phase of the study (HSSe). The skeletal muscle characterization carried out in this study included body composition and lean mass ascertained by dual-energy X-ray absorptiometry (DXA) scanning.

Fasting blood samples were taken from the antecubital fossa using vacutainer tubes and an indwelling 20 ga butterfly cannula. Blood was centrifuged at 4° C. 3000 rpm for 10 minutes and the serum was aliquoted and frozen at −80° C. until further analysis. Anthranilic acid and trigonelline levels in serum were measured by liquid chromatography followed by mass spectrometry (LC-MS/MS) at BEVITAL laboratories (Bergen, Norway).

The association between the ratio trigonelline:anthranilic acid and appendicular lean muscle mass index (ALMi; $kg/m^2$) was estimated by applying a regression adjusted for age after log 2 transformation of the serum concentration of the analytes.

Figure 10:
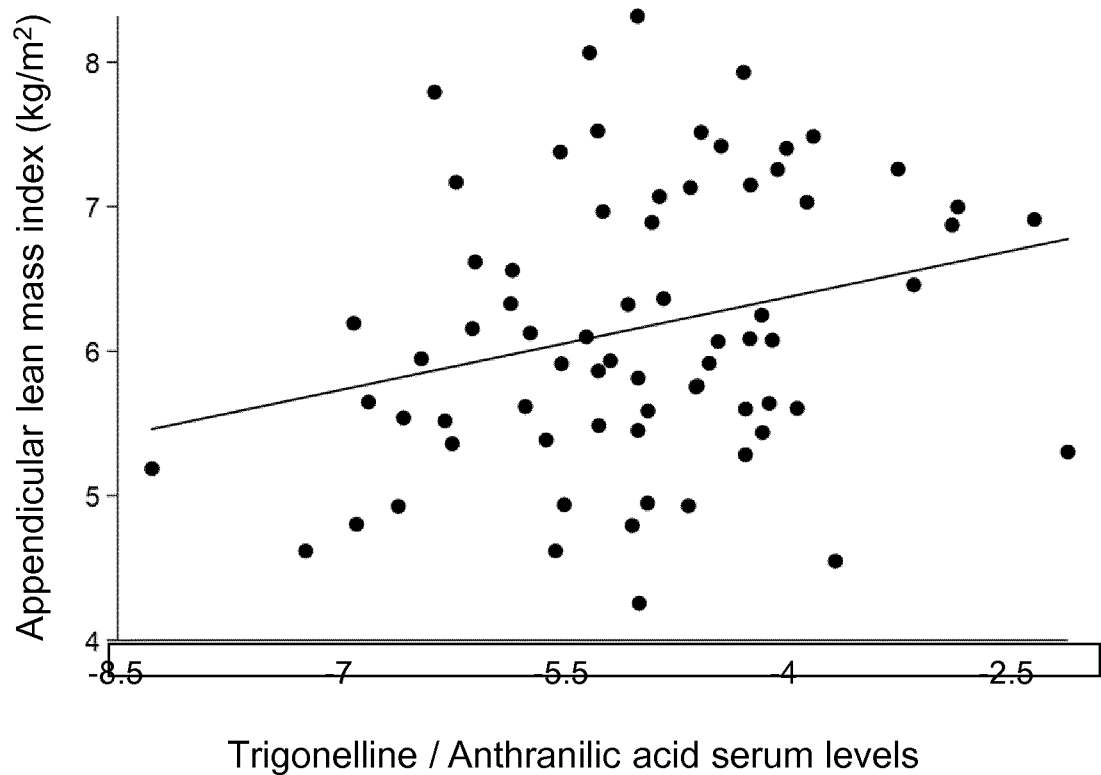
FIG. 10. Serum levels of trigonelline:anthranilic acid ratio positively associate with lean muscle mass index.

FIG. 10 shows that serum levels of trigonelline:anthranilic acid ratio are associated with lean muscle mass evaluated by the appendicular lean mass index. Levels of trigonelline and anthranilic acid were measured in the serum in a human cohort of 70 subjects, 52 females and 18 males, all aged 65 and above. The graph represents the association of the log 2 values the ratio of the analytes (trigonelline:anthranilic acid) in serum, x axis, with appendicular lean body mass index (ALMi) measured by DXA as surrogate for muscle mass, y axis. The line shows the fitted regression line of the ALMi on the log 2(trigonelline/anthranilic acid). According to the simple linear regression we obtained a Pearson correlation coefficient of 0.23, p-value=0.031; based on the regression adjusted for age we obtained an adjusted $R^2$ of 51% and a p-value=0.024 for the coefficient relative to the ratio of the analytes.

REFERENCES

Anders, S., Pyl, P. T., and Huber, W. (2015). HTSeq—a Python framework to work with high-throughput sequencing data. Bioinformatics 31, 166-169.

Anker, S. D., Morley, J. E., and von Haehling, S. (2016). Welcome to the ICD-10 code for sarcopenia. Journal of cachexia, sarcopenia and muscle 7, 512-514.

Chen, L. K., Liu, L. K., Woo, J., Assantachai, P., Auyeung, T. W., Bahyah, K. S., Chou, M. Y., Chen, L. Y., Hsu, P. S., Krairit, O., et al. (2014). Sarcopenia in Asia: consensus report of the Asian Working Group for Sarcopenia. Journal of the American Medical Directors Association 15, 95-101.

Clark R V, Walker A C, O'Connor-Semmes R L, Leonard M S, Miller R R, Stimpson S A, Turner S M, Ravussin E, Cefalu W T, Hellerstein M K, Evans W J. Total body skeletal muscle mass: estimation by creatine (methyl-d3) dilution in humans. J Appl Physiol (1985). 2014 Jun. 15; 116(12):1605-13.

Cruz-Jentoft, A. J., Baeyens, J. P., Bauer, J. M., Boirie, Y., Cederholm, T., Landi, F., Martin, F. C., Michel, J. P., Rolland, Y., Schneider, S. M., et al. (2010). Sarcopenia: European consensus on definition and diagnosis: Report of the European Working Group on Sarcopenia in Older People. Age Ageing 39, 412-423.

Dall, M., Penke, M., Sulek, K., Matz-Soja, M., Holst, B., Garten, A., Kiess, W., and Treebak, J T. Hepatic NAD(+) levels and NAMPT abundance are unaffected during prolonged high-fat diet consumption in C57B L/6JBomTac mice. Molecular and Cellular Endocrinology (2018) S0303-7207 (18) 30048.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Liu, R., Holik, A. Z., Su, S., Jansz, N., Chen, K., Leong, H. S., Blewitt, M. E., Asselin-Labat, M. L., Smyth, G. K., and Ritchie, M. E. (2015). Why weight? Modelling sample and observational level variability improves power in RNA-seq analyses. Nucleic acids research 43, e97.

Robinson, M. D., McCarthy, D. J., and Smyth, G. K. (2010). edgeR: a Bioconductor package for differential expression analysis of digital gene expression data. Bioinformatics 26, 139-140.

Smyth, G. K. (2004). Linear models and empirical bayes methods for assessing differential expression in microarray experiments. Statistical applications in genetics and molecular biology 3, Article 3.

Studenski S A, Peters K W, Alley D E, Cawthon P M, McLean R R, Harris T B, Ferrucci L, Guralnik J M, Fragala M S, Kenny A M, Kiel D P, Kritchevsky S B, Shardell M D, Dam T T, Vassileva M T (2014). The FNIH sarcopenia project: rationale, study description, conference recommendations, and final estimates. J Gerontol A Biol Sci Med Sci. 69(5), 547-558.

Stimpson S A, Leonard M S, Clifton L G, Poole J C, Turner S M, Shearer T W, Remlinger K S, Clark R V, Hellerstein M K, Evans W J. (2013) Longitudinal changes in total body creatine pool size and skeletal muscle mass using the $D_3$-creatine dilution method. J Cachexia Sarcopenia Muscle. June 25.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Wu, D., and Smyth, G. K. (2012). Camera: a competitive gene set test accounting for inter-gene correlation. Nucleic acids research 40, e133.

The invention claimed is:

1. A method of determining if a subject has sarcopenia or has an increased risk of developing sarcopenia comprising:
   (a) determining the levels of at least one of Trigonelline and Anthranilic acid in a sample obtained from the subject;
   (b) comparing the levels of at least one of Trigonelline and Anthranilic acid in the sample to a reference value;
   wherein the levels of at least one of Trigonelline and Anthranilic acid in the sample compared to the reference value is indicative of sarcopenia or risk of developing sarcopenia in the subject.

2. The method according to claim 1 wherein a decrease in a ratio of Trigonelline and Anthranilic acid in the sample from the subject compared to a reference value is indicative of sarcopenia or an increased risk of developing sarcopenia in the subject.

3. The method according to claim 1 wherein sarcopenia is characterized by one or more of low muscle mass, low muscle strength, and low physical performance.

4. The method according to claim 1 wherein the levels of Trigonelline and/or Anthranilic acid is determined by mass spectrometry.

5. The method according to claim 1 wherein the subject is a human subject.

6. A method of determining if a human subject has muscle wasting or a muscle disease, or has an increased risk of developing muscle wasting or a muscle disease comprising:
   (a) determining the level of Anthranilic acid and Trigonelline in a sample obtained from the human subject;
   (b) comparing the level of Anthranilic acid and Trigonelline in the sample to a reference value of Anthranilic acid and Trigonelline;
   wherein an increased level of Anthranilic acid in the sample compared to the reference value and a decreased level of Trigonelline in the sample compared to the reference value is indicative of muscle wasting or muscle disease, or risk of developing muscle wasting or muscle disease.

7. The method according to claim 5, wherein the human subject is an older adult or an elderly adult.

8. A method according to claim 1, wherein the reference value is determined from a sample obtained from the same subject or from a group of subjects.

9. The method according to claim 1 wherein the sample obtained from the subject is a blood derived sample.

10. The method according to claim 1 wherein the sample obtained from the subject is a urine sample.

11. A method for predicting the responsiveness to a nutritional composition of a subject having sarcopenia or having an increased risk of developing sarcopenia comprising:
   (a) detecting a level of one or more biomarker(s) in a sample obtained from the subject;
   (b) comparing the level of one or more biomarker(s) in the sample to a reference value;
   (c) predicting the responsiveness of the subject to the nutritional composition based on the results of step (b); and
   wherein said one or more biomarker(s) is Trigonelline and/or Anthranilic acid.

12. The method according to claim 11, wherein the biomarkers are Anthranilic acid and Trigonelline, and wherein the subject will be predicted to be responsive to the nutritional composition if the level of Anthranilic acid is increased in the sample compared to the reference value, and wherein the subject will be predicted to be responsive to the nutritional composition if the level of Trigonelline is decreased in the sample compared to the reference value.

13. The method according to claim 11, wherein a ratio of the levels of Trigonelline and Anthranilic acid are measured in the sample of the subject and compared to a reference value ratio of Trigonelline and Anthranilic acid, and wherein the subject will be predicted to be responsive to nutritional composition if the ratio of Trigonelline and Anthranilic acid is decreased in the sample compared to the reference value ratio.

14. The method according to claim 11, wherein the nutritional composition comprises Vitamin B3.

15. The method according to claim 11, wherein the nutritional composition comprises an NAD precursor.

16. The method according to claim 15, wherein the NAD precursor is nicotinamide riboside.

17. The method according to claim 11, wherein the biomarker is Trigonelline.

18. The method according to claim 17, wherein the nutritional composition comprises Trigonelline.

19. The method according to claim 17, wherein the nutritional composition comprises coffee extract.

* * * * *